United States Patent [19]

Brown et al.

[11] 4,206,218
[45] Jun. 3, 1980

[54] PHTHALIDYL ESTERS OF THE ACETONE ADDUCT OF EPICILLIN

[75] Inventors: William E. Brown, Princeton; Christopher M. Cimarusti, Hamilton, both of N.J.

[73] Assignee: E. R. Squibb & Sons, Inc., Princeton, N.J.

[21] Appl. No.: 938,663

[22] Filed: Aug. 31, 1978

[51] Int. Cl.$^2$ .................... A61K 31/43; C07D 499/68
[52] U.S. Cl. .................................. 424/271; 260/239.1
[58] Field of Search ...................... 260/239.1; 424/271

[56] References Cited

U.S. PATENT DOCUMENTS

| | | | |
|---|---|---|---|
| Re. 29,650 | 5/1978 | Ferres | 260/239.1 |
| 3,198,804 | 8/1965 | Johnson et al. | 260/239.1 |
| 3,485,819 | 12/1969 | Weisenborn et al. | 260/239.1 |
| 3,846,417 | 11/1974 | Atwal et al. | 260/243 C |
| 3,860,579 | 1/1975 | Ferres et al. | 260/239.1 |
| 3,951,954 | 4/1976 | Marakami et al. | 260/239.1 |
| 4,036,829 | 7/1977 | Ferres et al. | 260/239.1 |
| 4,072,677 | 2/1978 | Callander | 260/239.1 |

OTHER PUBLICATIONS

Clayton et al., J. Medicinal Chem. vol. 19, pp. 1385-1391, (1976).

Merck Index, 9th Ed. (1976) Entries 624, 3539, 4536, A14.

Primary Examiner—Norman Morgenstern
Assistant Examiner—Vera C. Clarke
Attorney, Agent, or Firm—Lawrence S. Levinson; Dale Lovercheck; Stephen B. Davis

[57] ABSTRACT

Penicillin esters and their acid addition salts of the formula

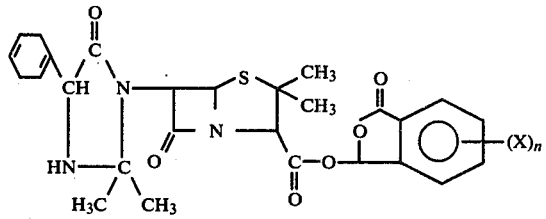

wherein X is hydrogen, methyl, methoxy, chloro, or bromo and n is an integer from 1 to 3 provided that n is 2 or 3 only when X is hydrogen or methoxy; are disclosed. Upon oral administration, these esters provide improved absorption and result in high concentrations of the antibacterially active parent penicillin in the blood, tissues and urine.

8 Claims, No Drawings

PHTHALIDYL ESTERS OF THE ACETONE ADDUCT OF EPICILLIN

BACKGROUND OF THE INVENTION

Epicillin, 6-[D-2-amino-2-(1,4-cyclohexadien-1-yl)acetamido]-3,3-dimethyl-7-oxo-4-thia-1-azabicyclo[3.2.0]heptane-2-carboxylic acid, is disclosed as a useful, orally administerable antibacterial agent by Weisenborn et al. in U.S. Pat. No. 3,485,819.

Talampicillin, 6-[D-2-amino-2-phenylacetamido]-3,3-dimethyl-7-oxo-4-thia-1-azabicyclo[3.2.0]heptane-2-carboxylic acid, 1,3-dihydro-3-oxo-1-isobenzofuranyl ester (i.e. the phthalidyl ester of ampicillin), is disclosed by Ferres et al. in U.S. Pat. No. 3,860,579. Talampicillin is stated to be well absorbed when administered orally and yield high serum levels of the parent penicillin, i.e. ampicillin.

Ferres in U.S. Pat. No. RE 29,650 describe the phthalidyl ester of 6-APA and various ampicillin intermediates wherein the α-amino group is protected.

Lactonyl esters of various penicillins and cephalosporins are disclosed by Ferres et al. in U.S. Pat. No. 4,036,829. Among the penicillins disclosed are the phthalidyl ester of hetacillin and various substituted pthalidyl esters of ampicillin.

Callander in U.S. Pat. No. 4,072,677 disclose a process for preparing various penicillin esters. Among the disclosed penicillin acyl sidechains is (α-aminocyclohexadienyl)acetamido and among the ester groups is phthalidyl.

Murakami et al. in U.S. Pat. No. 3,951,954 disclose oxofuryl esters of various penicillins and cephalosporins having an (α-amino-phenylacetamido) acyl sidechain. Among the compounds disclosed is the phthalidyl ester of ampicillin as note Example 4.

Hetacillin, 6-[2,2-dimethyl-5-oxo-4-phenyl-1-imidazolidinyl]-3,3-dimethyl-7-oxo-4-thia-1-azabicyclo[3.2.0]heptane-2-carboxylic acid, is disclosed by Johnson et al. in U.S. Pat. No. 3,198,804. Hetacillin is prepared by reacting ampicillin with acetone.

SUMMARY OF THE INVENTION

This invention is directed to phthalidyl penicillin esters of the formula

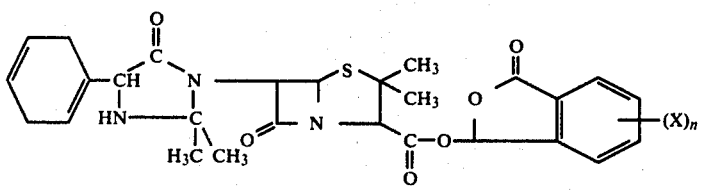

and acid addition salts thereof wherein X is hydrogen, methyl, methoxy, chloro, or bromo and n is an integer from 1 to 3 provided that n is 2 or 3 only when X is hydrogen or methoxy.

DETAILED DESCRIPTION

The ester products of formula I can be prepared by several methods. For example, epicillin can be reacted with acetone in the presence of triethylamine to yield the intermediate of the formula

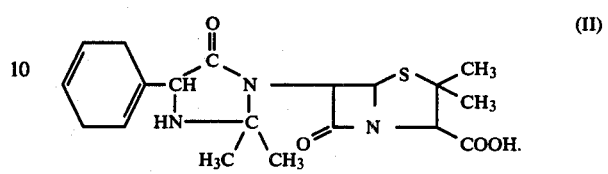

The intermediate of formula II can then be reacted with an isobenzofuran of the formula

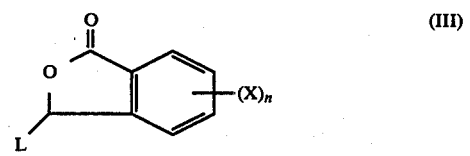

wherein L is hydroxy or bromo to yield the ester product of formula I.

The ester products of formula I can also be prepared by reacting epicillin with the isobenzofuran of formula III to yield the intermediate of the formula

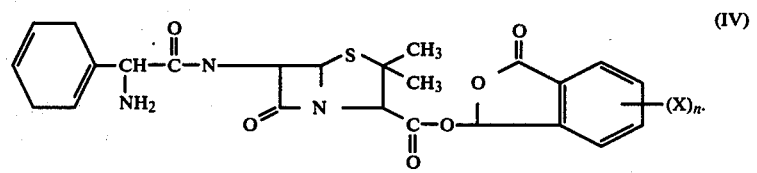

The intermediate of formula IV is then treated with acetone to yield the ester product of formula I.

The intermediate of formula IV can also be obtained by reacting the phthalidyl ester of 6-aminopenicillanic acid (6-APA) with an α-(protected amino)-1,4-cyclohexadienyl acylating agent followed by removal of the α-amino protecting group.

The ester products of formula I are conveniently isolated in the form of their acid addition salt. Acids useful for this purpose include inorganic acids such as hydrochloric, hydrobromic, sulfuric, nitric, and phosphoric acid, and organic acids such as maleic, fumaric, tartaric, citric, acetic, benzoic, 2-acetoxybenzoic, salicylic, succinic, nicotinic, methansulfonic, and cyclohexanesulfamic acid. These acid addition salts can be converted into the free form by reacting with a basic agent and, if desired, then converted to a different acid addition salt.

Preferred compounds of this invention are those of the formula

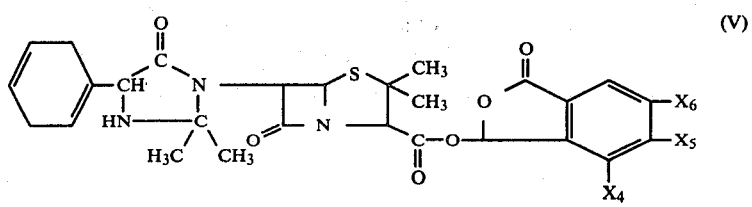

(V)

wherein $X_6$ is hydrogen, methoxy, bromo, or chloro; $X_5$ is hydrogen or methoxy provided that $X_5$ is methoxy only when $X_6$ is methoxy; and $X_4$ is hydrogen or methoxy provided $X_4$ is methoxy only when $X_6$ and $X_5$ are both methoxy.

Most preferred is the unsubstituted phthalidyl ester of formula V wherein $X_4$, $X_5$, and $X_6$ are all hydrogen.

The esters of formula I upon administration act as prodrugs of epicillin having the identical spectra of antibacterial activity. Thus, these esters are particularly useful in treating respiratory tract, gastrointestinal tract and genitourinary tract infections and skin and soft tissue infections due to susceptible strains of various gram-positive and gram-negative bacteria. Among the gram-positive bacteria that can be treated are beta-hemolytic streptococci, *Streptococcus viridans*, *Streptococcus faecalis*, *Diplococcus pneumonia*, *Staphylococcus albus*, and non-penicillanase producing strains of *Staphylococcus aureus* and among the gram-negative bacteria are *Escherichia coli*, *Proteus mirabilis*, *Hemophilus influenzae*, *Salmonella typhi*, *Salmonella paratyphi*, *Shigella* and *Neisseria gonorrhoeae*.

The esters of formula I are particularly useful when administered orally due to their improved rate of absorption. These esters provide higher concentrations of epicillin in the blood, tissues and urine then can be achieved by the oral administration of epicillin itself and they also decrease the incidence of gastrointestinal distress such as diarrhea and loose stools. The esters of formula I can be administered to the infected mammal in amounts ranging from about 15 to about 50 mg./kg./day in one or more doses. The amount of compound administered will vary, of course, depending upon the severity and nature of the infection; i.e. a urinary tract infection will in general require a higher does of antibacterial agent than a respiratory tract infection.

The esters of formula I and their acid addition salts are formulated for oral administration according to conventional pharmaceutical procedures. For example, the compounds can be encapsulated along with conventional excipients and preservatives, as may be necessary, so as to provide in a unitary dose the equivalent of 250 mg. or 500 mg. of epicillin. The compounds can also be formulated as a concentrate containing conventional excipients and flavoring agents which when reconstituted will provide a flavored suspension containing the equivalent of 125 mg. and 250 mg. of epicillin per 5 ml. teaspoonful. The compounds can also be formulated as pediatric drops which provide after reconstitution a flavored suspension containing the equivalent of 100 mg. of epicillin per one ml.

Illustrative process details are provided in the examples for the various reactions. All temperatures are on the centigrade scale.

EXAMPLE 1

6-[4-(1,4-Cyclohexadien-1-yl)-2,2-dimethyl-5-oxo-1-imidazolidinyl]-3,3-dimethyl-7-oxo-4-thia-1-azabicyclo[3.2.0]heptane-2-carboxylic acid, 1,3-dihydro-3-oxo-1-isobenzofuranyl ester, hydrochloride (1:1)

(a) 6-[4-(1,4-Cyclohexadien-1-yl)-2,2-dimethyl-5-oxo-1-imidazolidinyl]-3,3-dimethyl-7-oxo-4-thia-1-azabicyclo[3.2.0]heptane-2-carboxylic acid A suspension of 10 g. of epicillin in 50 ml. of acetone (previously dried over Linde 4A molecular sieves) is stirred with 7 ml. of triethylamine for 24 hours at 25° and an additional 24 hours at 30°. The resulting solution is filtered and added dropwise to 50 ml. of water maintained at 0°-10° and pH 2.5-3.0 by the simultaneous addition of cold 30% sulfuric acid solution. The resulting slurry is stirred for 2 hours at 0° and pH 2.55 and is then filtered. The crystalline product is washed with 20 ml. of cold water and dried at 40°-50° over $P_2O_5$ in vacuo to yield 6.19 g. of 6-[4-(1,4-cyclohexadien-1-yl)-2,2-dimethyl-5-oxo-1-imidazolidinyl]-3,3-dimethyl-7-oxo-5-thia-1-azabicyclo[3.2.0]heptane-2-carboxylic acid; m.p. 186° (dec., browns at 174°).

Analysis Calculated for $C_{19}H_{25}SN_3O_4$: C, 58.29; H, 6.44; N, 10.73; S, 8.19. Found: C, 58.06; H, 6.52; N, 10.62; S 7.99.

(b) 6-[4-(1,4-Cyclohexadien-1-yl)-2,2-dimethyl-5-oxo-1-imidazolidinyl]-3,3-dimethyl-7-oxo-4-thia-1-azabicyclo[3.2.0]-heptane-2-carboxylic acid, 1,3-dihydro-3-oxo-1-isobenzofuranyl ester, hydrochloride (1:1)

A mixture of 14.81 g. (0.0378) mole) of the acid product from part (a) and 5.3 ml. (0.0378 mole) of triethylamine in 265 ml. of acetone (previously dried over Linde 4A molecular sieves) is stirred at room temperature for 30 minutes. 3.78 g. of potassium bicarbonate and 8 g. of 3-bromophthalide are added. After four hours, the resulting mixture is filtered and the filtrate is concentrated in vacuo to about 9.5 ml. 375 ml. of ethyl acetate is added and the resulting solution is washed with 2% sodium bicarbonate solution (2×40 ml.), water (2×40 ml.), dried, and concentrated to yield 19.89 g. of crude product. This crude material is passed through a column containing 800 g. of silica gel (sili CAR CC-7) and eluted with (1:1) EtOAc:benzene to give one fraction containing 3.55 g. of product and a second fraction containing 8.34 g. of purer product. The 8.34 g. purer fraction is dissolved in 140 ml. of (1:1) EtOAc:ethyl ether and 1.66 mmoles/ml. of HCl solution in ethyl ether (as determined by trituration) is added. The HCl salt product is filtered immediately, washed with ether and dried overnight without heating to yield 8.33 g. of 6-[4-(1,4-cyclohexadien-1-yl)-2,2-dimethyl-5-oxo-1-imidazolidinyl]-3,3-dimethyl-7-oxo-4-thia-1-azabicyclo[3.2.0]heptane-2-carboxylic acid, 1,3-dihydro-3-oxo-1-isobenzofuranyl ester, hydrochloride (1:1); m.p. 160°-162°.

Analysis: Calculated for $C_{27}H_{29}N_3O_6S \cdot HCl$: C, 57.90; H, 5.40; S, 5.72; Cl, 6.33; N, 7.50 Found: C, 57.01; H, 5.78; S, 5.61; Cl, 5.93; N, 7.25.

EXAMPLES 2-10

Following the procedure of Example 1 but employing the substituted isobenzofuran shown in Col. I one obtains the phthalidyl ester product shown in Col. II.

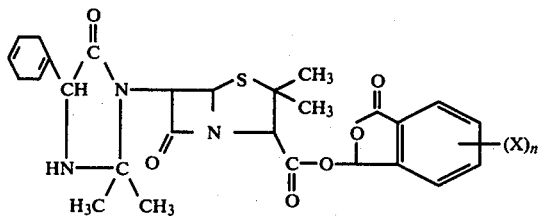

| Ex. | $X_4$ | $X_5$ | $X_6$ | $X_7$ |
|---|---|---|---|---|
| 2 | H | H | $CH_3$ | H |
| 3 | H | H | $OCH_3$ | H |
| 4 | H | H | Br | H |
| 5 | H | H | Cl | H |
| 6 | H | $OCH_3$ | $OCH_3$ | H |
| 7 | $OCH_3$ | $OCH_3$ | $OCH_3$ | H |
| 8 | Cl | H | H | H |
| 9 | $OCH_3$ | H | H | H |
| 10 | $CH_3$ | H | H | H |

What is claimed is:

1. A compound of the formula:

wherein X is hydrogen, methyl, methoxy, bromo, or chloro; n is an integer from 1 to 3 provided that n is 2 or 3 only when X is hydrogen or methoxy; and a pharmaceutically acceptable acid addition salt thereof.

2. The compound of claim 1 having the formula:

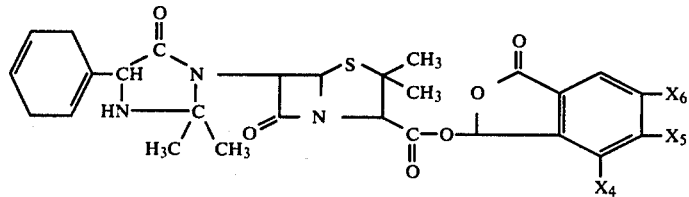

wherein $X_6$ is hydrogen, methoxy, bromo, or chloro; $X_5$ is hydrogen or methoxy provided that $X_5$ is methoxy only if $X_6$ is methoxy; $X_4$ is hydrogen or methoxy provided that $X_4$ is methoxy only if both $X_5$ and $X_6$ are methoxy; and a pharmaceutically acceptable acid addition salt thereof.

3. The compound of claim 2 wherein $X_4$, $X_5$, and $X_6$ are all hydrogen.

4. The hydrochloride salt of claim 3.

5. An antibacterial pharmaceutical composition comprising a pharmaceutically acceptable carrier and as the active antibacterial agent one or more of the ester compounds of claim 1.

6. The compositon of claim 5 wherein the antibacterial agent is 6-[4-(1,4-cyclohexadien-1-yl)-2,2-dimethyl-5-oxo-1-imidazolidinyl]-3,3-dimethyl-7-oxo-4-thia-1-azabicyclo[3.2.0]heptane-2-carboxylic acid, 1,3-dihydro-3-oxo-1-isobenzofuranyl ester.

7. The method of treating a bacterial infection in a mammalian species which comprises orally administering an effective amount of the composition of claim 5.

8. The method of treating a bacterial infection is a mammalian species which comprises orally administering an effective amount of the composition of claim 6.

* * * * *

UNITED STATES PATENT AND TRADEMARK OFFICE
CERTIFICATE OF CORRECTION

PATENT NO. : 4,206,218
DATED : June 3, 1980
INVENTOR(S) : William E. Brown et al.

It is certified that error appears in the above-identified patent and that said Letters Patent are hereby corrected as shown below:

Col. 2, structure (IV), the portion "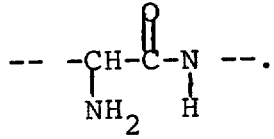" should read:

-- -CH-C-N --.
   |  ‖  |
   NH₂ O H (with structure showing $-\underset{NH_2}{CH}-\underset{\parallel}{\overset{O}{C}}-\underset{H}{N}-$)

Col. 3, line 45, change "does" to -- dose --.
Col. 6, line 48, change "is" to -- in --.

Signed and Sealed this

Twenty-third Day of September 1980

[SEAL]

Attest:

SIDNEY A. DIAMOND

Attesting Officer

Commissioner of Patents and Trademarks